Nov. 7, 1961 D. H. MOREY, JR Plant Pat. 2,103
ROSE PLANT
Filed Dec. 14, 1960
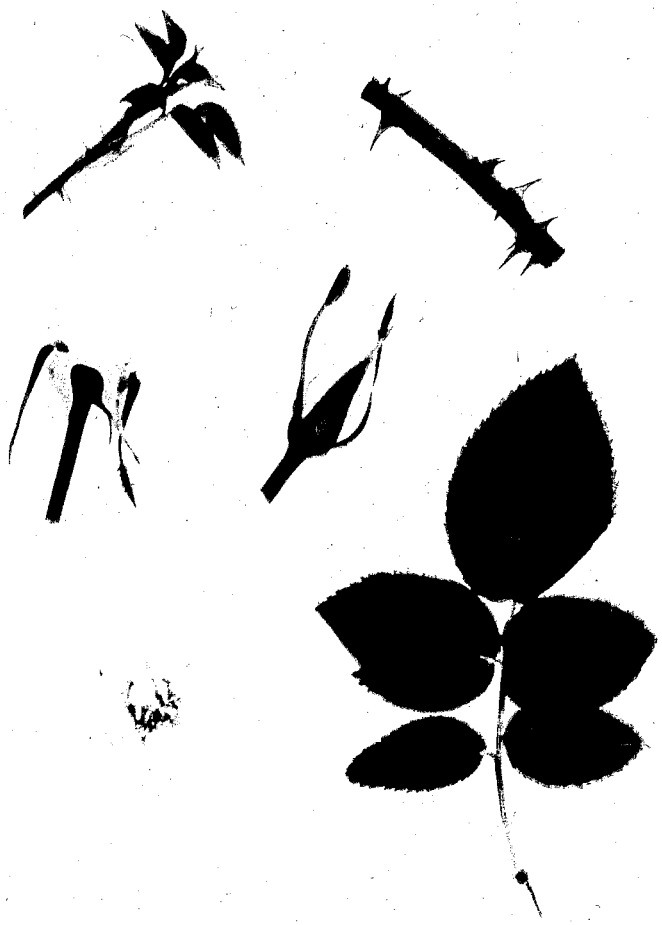
Inventor.
Dennison H. Morey, Jr.
By: Robb & Robb
Attorneys United States Patent Office Plant Pat. 2,103
Patented Nov. 7, 1961

2,103
ROSE PLANT

Dennison H. Morey, Jr., Pleasanton, Calif., assignor to Jackson & Perkins Company, Newark, N.Y., a corporation of New York Filed Dec. 14, 1960, Ser. No. 75,896
1 Claim. (Cl. 47—61)

The present invention relates to a new and distinct variety of rose plant of the hybrid tea class, which was originated by me by crossing the variety "Golden Masterpiece" (Plant Patent No. 1,284) with the variety "Lydia" (unpatented).

The primary objective of this breeding was to produce a new rose variety comparable to the parent variety "Golden Masterpiece," but in which the flower color is intensified without reducing the flower size. This objective was substantially achieved, along with other desirable improvements, although the flower size in the new variety is slightly less than that of "Golden Masterpiece," as evidenced by the following unique combination of characteristics which are outstanding in the new variety and which distinguish it from its parents, as well as from all other varieties of which I am aware:

(1) A vigorous and upright habit of growth throughout the season;

(2) A free blooming habit;

(3) An ovoid bud form;

(4) Relatively large high-centered flowers ranging from 5 to 6 inches in diameter and each having from 35 to 40 petals;

(5) A clear and distinctive Apricot Yellow general color tonality of the flowers, with the upper half of the petals lightly overcast with Empire Yellow; and (6) Distinctive Grenadine Red stamens and Begonia Rose filaments.

Asexual reproduction of the new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Golden Masterpiece."
*Pollen parent.*—"Lydia."
Classification:
*Botanic.*—Hybrid tea.
*Commercial.*—Hybrid tea.

*Flower*

(Observations made from specimens grown outdoors at Newark, New York, in the early part of the month of September.)

Blooming habit: Recurrent—continuous.
Bud:
*Size.*—Medium.
*Form.*—Ovoid; is not affected by wet or hot weather.
*Color.*—When sepals first divide—Pale Lemon Yellow, Plate 4. When petals begin to unfurl—Light Cadmium, Plate 4. When half-blown: inside of petals—Empire Yellow, Plate 4, with upper half of petals overcast with Pinard Yellow, Plate 4; reverse of petals—Pinard Yellow, Plate 4.
*Sepals.*—Slightly branched; curl back when petals begin to unfurl. Color: inside—Absinthe Green, Plate 31; outside—Biscay Green, Plate 17.
*Calyx.*—Color.—Parrot Green, Plate 6. Shape—apple. Size—Small. Aspect—smooth. Odor when rubbed—none.
*Peduncle.* — Length — medium. Aspect — rough. Strength—erect; slender. Color—Cress Green, Plate 31.
*Opening.*—Opens up well; is not affected by adverse weather conditions.
Bloom:
*Size.*—Large. Average size when fully expanded—from 5 inches to 6 inches.
*Borne.*—Singly.
*Stems.*—Medium length; strong.
*Form (when first open).*—High-centered. Permanence—retains its form to the end.
*Petalage.*—Double (full but open center). Number of petals under normal conditions—from 35 to 40.
*Color.*—Center of flower—Apricot Yellow, Plate 4. Outer petals—lower half of petals Empire Yellow, Plate 4, and upper half of petals Pinard Yellow, Plate 4. Base of petals (aiglet)—Lemon Chrome, Plate 4. Inside of petals—Apricot Yellow, Plate 4, with upper half of petals lightly overcast with Empire Yellow, Plate 4. Reverse of petals—Pinard Yellow, Plate 4. General tonality from a distance—Empire Yellow, Plate 4.
*Discoloration.*—General tonality at end of first day—Apricot Yellow, Plate 4, very lightly overcast with Empire Yellow, Plate 4. Second day—Apricot Yellow, Plate 4, lightly overcast with Empire Yellow, Plate 4. Third day—Empire Yellow, Plate 4.
Petals:
*Texture.*—Leathery; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; many; regularly arranged around styles. Color—Grenadine Red, Plate 2.
Stamens, filaments (threads): Medium length. Color—Begonia Rose, Plate 1.
Pollen: Color—Safrano Pink, Plate 2.
Styles: Bunched; uneven length; medium length; thin.
Stigmas: Color—Bittersweet Pink, Plate 2.
Ovaries: All enclosed in calyx.
Hips: None.
Seeds: None.

*Plant*

Form: Bush.
Growth: Vigorous (attains height of 6 feet); upright.
Foliage: Compound of 3–5 leaflets.
*Size.*—Large.
*Quantity.*—Normal.
*Color.*—New foliage: upper side—Lettuce Green, Plate 5, lightly overcast with Carmine, Plate 1; under side—Carmine, Plate 1. Old foliage: upper side—Cress Green, Plate 31; under side—Light Cress Green, Plate 31.

*Shape.*—Oval pointed.

*Texture.*—Upper side—leathery; glossy. Under side—smooth.

*Ribs and veins.*—Ordinary.

*Edge.*—Serrated (saw-toothed).

*Serration.*—Both double and single; small.

*Leaf stem.*—Color—Chromium Green, Plate 32. Under side—Prickly.

*Stipules.*—Medium length; smooth.

Wood:

*New wood.*—Color—Grass Green, Plate 6. Bark—smooth.

*Old wood.*—Color—Elm Green, Plate 17. Bark—smooth.

Thorns:

*Thorns.*—Quantity: on main stalks from base—ordinary; on laterals from stalk—ordinary. Form—narrow base; medium length; straight. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous and upright habit of growth throughout the season, a free blooming habit, an ovoid bud form, relatively large and high-centered flowers, a clear and distinctive Apricot Yellow general color tonality of the flowers, with the upper half of the flower petals lightly overcast with Empire Yellow color, and distinctive Grenadine Red stamens and Begonia Rose filaments.

No references cited.